United States Patent
Kozyuk et al.

(10) Patent No.: US 9,777,292 B2
(45) Date of Patent: Oct. 3, 2017

(54) METHODS FOR TREATING BIOSOLIDS SLUDGE WITH CAVITATION

(71) Applicant: Arisdyne Systems, Inc., Cleveland, OH (US)

(72) Inventors: Oleg Kozyuk, North Ridgeville, OH (US); Peter Reimers, Shaker Heights, OH (US)

(73) Assignee: ARISDYNE SYSTEMS, INC., Cleveland, OH (US)

( * ) Notice: Subject to any disclaimer, the term of this patent is extended or adjusted under 35 U.S.C. 154(b) by 97 days.

(21) Appl. No.: 14/551,625

(22) Filed: Nov. 24, 2014

(65) Prior Publication Data

US 2015/0158752 A1 Jun. 11, 2015

Related U.S. Application Data

(60) Provisional application No. 61/912,203, filed on Dec. 5, 2013.

(51) Int. Cl.
*C02F 3/00* (2006.01)
*C12P 3/00* (2006.01)
(Continued)

(52) U.S. Cl.
CPC .............. *C12P 3/00* (2013.01); *C02F 11/04* (2013.01); *C02F 11/18* (2013.01); *C12P 5/023* (2013.01);
(Continued)

(58) Field of Classification Search
CPC .... B01F 3/04; B09C 1/002; B09C 1/10; B01J 19/06; C02F 1/02; C02F 1/025;
(Continued)

(56) References Cited

U.S. PATENT DOCUMENTS 5,492,654 A * 2/1996 Kozjuk ................ B01F 5/0656
261/76
5,969,207 A 10/1999 Kozyuk
(Continued)

FOREIGN PATENT DOCUMENTS

EP 1559688 A1 8/2005
KR 101317490 10/2013
(Continued)

OTHER PUBLICATIONS

Novak, et. al., A New Solids Technology Train: Can 70% Volatile Solids Reduction and Class A Biosolids be Achieved from Digestion; WEFTEC 2009, Water Environment Federation.
(Continued)

*Primary Examiner* — Dirk Bass
*Assistant Examiner* — Hayden Brewster
(74) *Attorney, Agent, or Firm* — Pearne & Gordon LLP (57) ABSTRACT

Described herein are processes for increasing biogas yield and reducing volatile solids in biosolids sludge. The biosolids sludge is passed through a controlled flow, hydrodynamic cavitation apparatus and further subjected to anaerobic digestion. The biosolids sludge can be treated with hydrodynamic cavitation prior to or after the sludge is exposed to a thermal hydrolysis step to hydrolyze the sludge.

16 Claims, 5 Drawing Sheets

(51) Int. Cl.
*C12P 5/02* (2006.01)
*C02F 11/04* (2006.01)
*C02F 11/18* (2006.01)
*B01J 3/00* (2006.01)
*C02F 9/00* (2006.01)
*C12P 23/00* (2006.01)
*C02F 1/34* (2006.01)
*C02F 11/12* (2006.01)

(52) U.S. Cl.
CPC ............... *C02F 1/34* (2013.01); *C02F 11/12* (2013.01); *C02F 2303/06* (2013.01); *Y02E 50/343* (2013.01)

(58) Field of Classification Search
CPC ...... C02F 1/24; C02F 1/34; C02F 3/00; C02F 3/006; C02F 3/12; C02F 3/18; C02F 3/26; C02F 3/28; C02F 3/34; C02F 9/00; C02F 2101/32; C12M 21/04; C12P 5/02; C12P 5/023; C12P 23/00; Y02E 50/343
USPC ................. 210/600, 601, 609; 261/76; 366/366–368; 435/167
See application file for complete search history.

(56) References Cited

U.S. PATENT DOCUMENTS

| | | | |
|---|---|---|---|
| 6,444,124 | B1 | 9/2002 | Onyeche et al. |
| 7,163,629 | B2 | 1/2007 | Abu-Orf et al. |
| 7,651,614 | B2 | 1/2010 | Kelsey et al. |
| 7,667,082 | B2 | 2/2010 | Kozyuk |
| 8,052,872 | B2 | 11/2011 | Walton et al. |
| 8,603,339 | B2 | 12/2013 | Maeda et al. |
| 2004/0256314 | A1 | 12/2004 | Schmid et al. |
| 2008/0217211 | A1 | 9/2008 | Chornet et al. |
| 2009/0200231 | A1* | 8/2009 | Walton ............... C02F 1/008 210/631 |
| 2010/0300966 | A1* | 12/2010 | Kelsey ................ C02F 1/34 210/622 |
| 2012/0181216 | A1 | 7/2012 | Kozyuk et al. |
| 2013/0062249 | A1 | 3/2013 | Kozyuk et al. |
| 2014/0069875 | A1* | 3/2014 | Rippetoe ............. B09C 1/00 210/748.1 |
| 2014/0246369 | A1* | 9/2014 | Stephenson ........ C02F 3/1221 210/605 |

FOREIGN PATENT DOCUMENTS

| | | |
|---|---|---|
| KR | 2013-0129564 A | 11/2013 |
| KR | 20130129564 | 11/2013 |
| WO | 2013039759 | 3/2013 |

OTHER PUBLICATIONS

Partial supplementary European Search Report issued in corresponding European Patent Application No. 14867398.1; dated May 29, 2017.

* cited by examiner

METHODS FOR TREATING BIOSOLIDS SLUDGE WITH CAVITATION

This application claims the benefit of U.S. provisional application Ser. No. 61/912,203 filed Dec. 5, 2013, the contents of which are incorporated herein in their entirety by reference.

FIELD

The invention relates to processes for treating biosolids sludge with hydrodynamic cavitation, and more particularly, processes for increasing biogas yield and reducing volatile solids in biosolids sludge with the use of hydrodynamic cavitation.

BACKGROUND

Wastewater is generated from a variety of municipal, commercial, and industrial sources. Prior to environmental regulations, wastewater was discharged into waterways and landfills. Wastewater sludge, also generated at a wastewater treatment facility, may undergo additional treatment.

Wastewater treatment facilities are treating the wastewater sludge to produce biogas and biosolids from anaerobic digestion, a naturally-occurring process. The biogas generated includes a blend of methane and carbon dioxide gas that may be used as fuel, and biosolids generated from the anaerobic digestion are nutrient-rich organic materials that may be used as fertilizers. The anaerobic digestion process occurs in three phases: hydrolysis, fermentation, and biogas formation.

Although naturally-occurring, biological materials may be more easily degraded than others. To increase biological degradation of the wastewater sludge to form a hydrolyzed sludge, thermal hydrolysis may be used as the first step of anaerobic digestion, where thermal hydrolysis is a two-stage process that combines pressure cooking and rapid decompression. As a result of thermal hydrolysis, hydrolyzed sludge is more biodegradable, which results in a greater production of biogas and biosolids.

Processes for improving the yield of biogas and reducing volatile solids in biosolids sludge are needed in addition to other improvements, such as thermal hydrolysis. The processes disclosed herein achieve desired enhancement of biosolids sludge treatment.

SUMMARY

Described herein are processes for treating biosolids sludge. In an embodiment, a process for treating biosolids sludge can include providing a controlled flow, hydrodynamic cavitation apparatus having a local constriction. To treat the biosolids sludge, a stream of the sludge is passed through the local constriction of the controlled flow, hydrodynamic cavitation apparatus to form hydrodynamic cavitation zone downstream of the local constriction, wherein the hydrodynamic cavitation zone contains cavitation bubbles, which can be maintained in the hydrodynamic cavitation zone for less than 0.01 second. The cavitation bubbles are collapsed under static pressure of at least 30 psi to form a treated biosolids sludge that can be further subjected to process steps.

The local constriction of the cavitation apparatus can be an orifice, baffle, bluff body or nozzle. The biosolids sludge can be passed through the orifice, baffle or nozzle to create a pressure differential across the orifice of at least 150 psi. Prior to passing through the local constriction, the biosolids sludge can be at a pressure of at least 175 psi.

In one embodiment, the controlled flow, hydrodynamic cavitation apparatus can be a static cavitation apparatus and the sludge can be treated in the absence of ultrasonic cavitation.

The biosolids sludge being treated can be a dewatered biosolids sludge, for example, from a waterwork or wastewater treatment plant. The dewatered sludge can be subjected to thermal hydrolysis prior to being passed through the local constriction of the controlled flow, hydrodynamic cavitation apparatus. In another embodiment, the treated biosolids sludge being subjected to thermal hydrolysis, anaerobic digestion or a combination of both.

The biosolids sludge being subjected to anaerobic digestion to produce biogas, the biogas including carbon dioxide and methane, wherein the treated biosolids sludge produces at least 15 percent more biogas as compared to untreated biosolids sludge being subjected to the anaerobic digestion. In another embodiment, the treated biosolids sludge being subjected to anaerobic digestion to reduce volatile solids in the treated biosolids sludge, wherein the treated biosolids sludge produces at least 2 percent less volatile solids as compared to untreated biosolids sludge being subjected to the anaerobic digestion.

In another process for treating dewatered biosolids sludge from a waterwork or wastewater treatment plant, a static controlled flow, hydrodynamic cavitation apparatus having a local constriction can be provided for passing the dewatered biosolids sludge through the local constriction of the static controlled flow, hydrodynamic cavitation apparatus to form hydrodynamic cavitation zone containing cavitation bubbles. The dewatered biosolids sludge can be passed through the local constriction to create a pressure differential across the local constriction of at least 150 psi. The cavitation bubbles are collapsed under static pressure to form a treated biosolids sludge.

The static controlled flow, hydrodynamic cavitation apparatus can have at least two local constrictions in series and the dewatered biosolids sludge can be passed through the at least two local constrictions. In an alternative embodiment, the dewatered biosolids sludge can be passed through the local constriction at least two times. The local constrictions can be an orifice, baffle or nozzle.

The treated dewatered biosolids sludge can be subjected to thermal hydrolysis, anaerobic digestion or a combination of both. In one instance, the treated biosolids sludge can be subjected to anaerobic digestion to produce biogas, the biogas including carbon dioxide and methane, wherein the treated biosolids sludge produces at least 15 percent more biogas as compared to untreated dewatered biosolids sludge being subjected to the anaerobic digestion. In another instance, the treated biosolids sludge can be subjected to anaerobic digestion to reduce volatile solids in the treated biosolids sludge, wherein the treated biosolids sludge produces at least 2 percent less volatile solids as compared to untreated dewatered biosolids sludge being subjected to the anaerobic digestion.

DETAILED DESCRIPTION

Herein, when a range such as 5-25 (or 5 to 25) is given, this means preferably at least or more than 5 and, separately and independently, preferably not more than or less than 25. In an example, such range defines independently not less than 5, and separately and independently, not more than 25.

A process has been discovered for an efficient, cost-effective wastewater sludge or biosolids sludge treatment process by using controlled flow, hydrodynamic cavitation at various points of a biosolids sludge treatment system, for example, prior to anaerobic digestion. It has been found that selective use of controlled flow, hydrodynamic cavitation can improve biogas production from the biosolids sludge and result in a reduction of volatile solids in the sludge. While processing sludge by thermal hydrolysis, the controlled flow cavitation device can increase the biodegradability of the sludge and thus biogas production. The pressure generated in the controlled flow cavitation device will further break down sludge by destroying agglomerates, cell structures, and even cell walls. By further breaking down the sludge, improved yields are achieved through thermal hydrolysis by increasing the digestibility of biomass in anaerobic fermentation. Using the controlled flow cavitation device, sludge is made less viscous.

Figure 1:
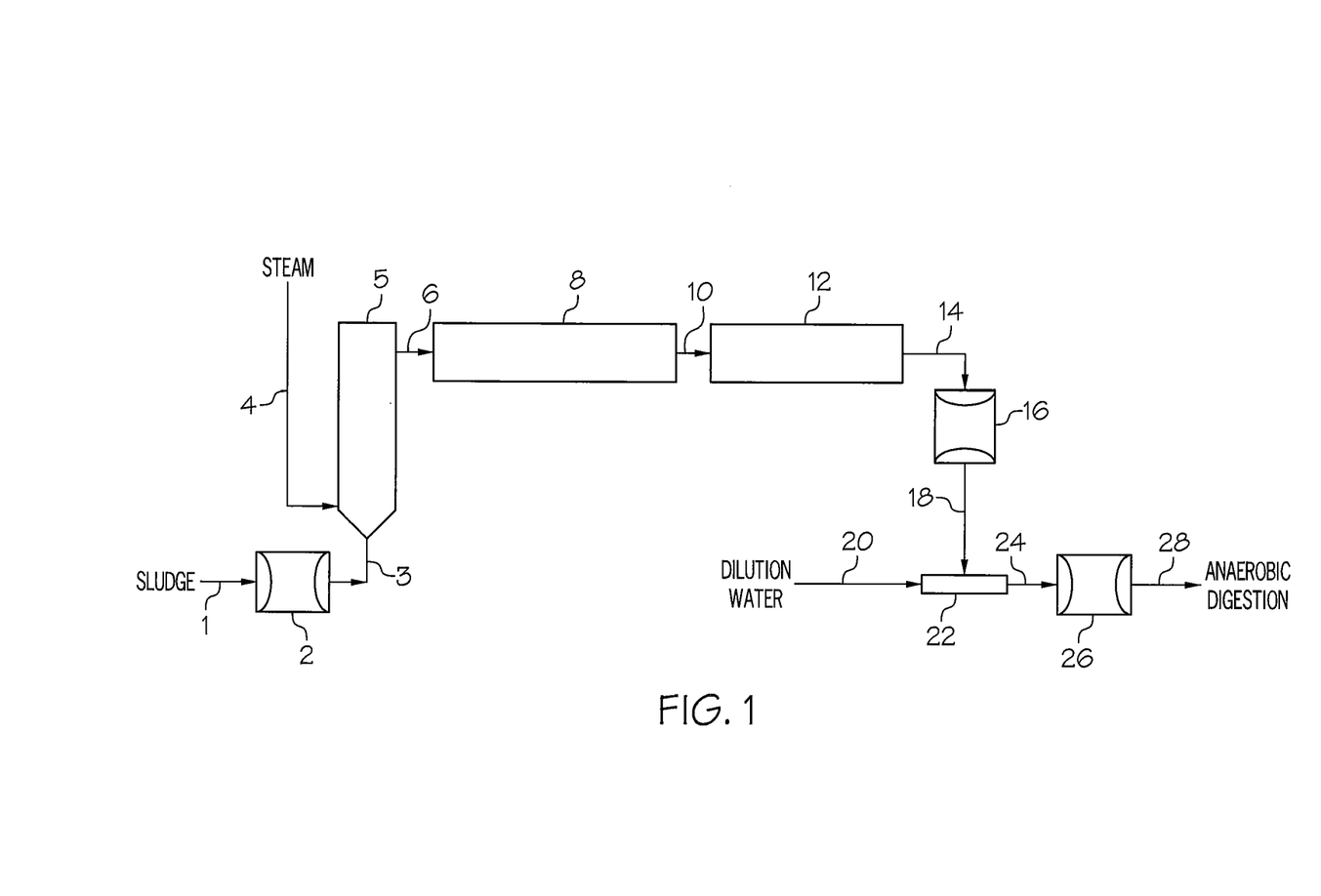
FIG. 1 is a flow diagram of a biosolids sludge treatment system utilizing thermal hydrolysis and hydrodynamic cavitation.

FIG. 1 shows a sludge treatment system utilizing thermal hydrolysis and hydrodynamic cavitation at various points of the system prior to anaerobic digestion. Biosolids sludge 1 can be treated by passing the sludge 1 through a controlled flow, hydrodynamic cavitation apparatus 2. The sludge 1 may enter the controlled flow, hydrodynamic cavitation apparatus 2 to increase the localized temperature and pressure of the sludge and break up materials and increase available sites for reaction under thermal hydrolysis. Alternatively, the biosolids sludge 1 can be fed directly to a thermal hydrolysis process prior to being subjected to hydrodynamic cavitation. As shown in FIG. 1, one or more controlled flow, hydrodynamic cavitation apparatuses (e.g., 2), either individually or in combination, can be used in a sludge treatment system.

The biosolids sludge 1 being treated can be from a waterwork, industrial or wastewater treatment plant. In an example, the biosolids sludge can be a dewatered biosolids sludge stream. The biosolids sludge 1 can be supplied to the apparatus 2 from a storage silo or hopper by a pump, such as a progressive cavity pump. The biosolids sludge 1 may contain enzymes used to facilitate the thermal hydrolysis process. The sludge 1 can be at a temperature in the range to 10 to 60° C.

The sludge 1 can be passed through a controlled flow, hydrodynamic cavitation apparatus 2 to induce cavitation. Flow into the controlled flow cavitation apparatus can be provided with fluid pumping devices as known in the art, such as a pump, centrifugal pump, positive-displacement pump or diaphragm pump. An auxiliary pump can provide flow under a static pressure $P_1$ to the apparatus 2. As discussed herein, pressure $P_1$ is defined as the processing pressure for the controlled flow cavitation apparatus. The processing pressure is preferably at least 150, 170, 200, 300, 400, 500, 600, 700, 800, 850, 900, or 1000, psi.

The apparatus 2 can form a hydrodynamic cavitation zone downstream of a local constriction in the apparatus 2. The hydrodynamic cavitation zone can contain cavitation bubbles. In general, cavitation can be described as the generation, subsequent growth and collapse of cavitation bubbles and cavities. During the collapse of the cavitation bubbles, high-localized pressures and temperatures are achieved, with some estimations of 5000° C. and pressure of approximately 500 kg/cm$^2$ (K. S. Suslick, Science, Vol. 247, 23 Mar. 1990, pgs. 1439-1445). High temperatures and pressures can stimulate the progress of various chemical reactions which may not be possible under ordinary conditions, such as standard temperature and pressure, STP. Therefore, a material may undergo physical changes under the influence of cavitation energy. Specifically, cell structures and organic materials may be disintegrated, and naturally occurring cell polymers may be dissolved. For example, forces obtained from cavitation are used to disaggregate, disassociate, shake off and/or strip away molecules, as well as disassociate tightly packed molecules to make them more accessible to an enzyme for subsequent enzymatic treatment.

The local constriction in the controlled flow, hydrodynamic cavitation apparatus can be an orifice, baffle, bluff body or nozzle. The orifice can be any shape, for example, cylindrical, conical, oval, right-angled, square, etc. Depending on the shape of the orifice, this determines the shape of the cavitation fluid jets flowing from the localized flow constriction. The orifice can have any diameter, for example, the diameter can be greater than 0.1, 1, 2, 3, 5, or 10 mm, and preferably more than 3 mm. In one example, the diameter of the orifice can be about 3 mm or about 4 mm. For multi-stage cavitation, two or more local constrictions, such as an orifices, can be in series, for example at least 2, 3, 4 or 5 orifices can be in series.

Preferably, the controlled flow, hydrodynamic cavitation apparatus is a static device that produces cavitation by passive means. Examples of static cavitational energy sources that can be used to apply cavitational energy to the sludge include, but are not limited to, static mixers, orifice plates, perforated plates, nozzles, venturis, jet mixers, eductors, cyclonettes (e.g., Fluid-Quip, Inc.), and control flow cavitation devices (e.g., Arisdyne Systems, Inc.), such as those described in U.S. Pat. Nos. 5,810,052; 5,931,771; 5,937,906; 5,971,601; 6,012,492; 6,502,979; 6,802,639; 6,857,774 and 7,667,082.

The hydrodynamic cavitation zone downstream of the local constriction is generated as the processing pressure of the biosolids sludge is reduced after passing through the local constriction. Maintaining a pressure differential across the local constriction allows control of the cavitation intensity in the apparatus 2. The pressure differential across the local constriction is preferably at least 150, 170, 200, 300, 400, 500, 600, 700, 800, 850, 900, or 1000, psi. Velocity of biosolids sludge through the local constriction in the controlled flow cavitation apparatus is preferably at least 1, 5, 10, 15, 20, 25, 30, 40, 50, 60 or 70 meters per second (m/s).

The cavitation bubbles formed by passing the biosolids sludge through the local constriction of the controlled flow, hydrodynamic cavitation apparatus are collapsed under the influence of static pressure $P_2$. Energy emitted during collapse of the cavitation bubbles is directly proportional to magnitude of static pressure in surrounding liquid bubbles. Therefore, magnitude of $P_2$, is directly related to energy emitted during cavitation bubbles collapse and better dispersion effect. As the magnitude of $P_2$ increases, the severity or hardness of collapse of each cavitation bubble separately increases, as well as the energy dissipated due to the decrease of the volume in which these cavitation bubbles collapse. The static pressure is preferably at least 30, 40, 50, 60, 70, 80, 90, 100, 150, 200, 250 or 300 psi. The collapsing of the cavitation bubbles in the hydrodynamic cavitation zone forms a treated biosolids sludge stream 3.

The biosolids sludge can be passed through the controlled flow, hydrodynamic cativation apparatuses described herein as a single pass process or a multi-pass process to subject the sludge to more than one hydrodynamic cavitation. To create a multi-pass cavitation process the biosolids sludge can be recycled repeatedly through the apparatus via a recirculation loop. For example, the biosolids sludge can pass through the controlled flow, hydrodynamic cavitation apparatus at least 2, 3, 4 or 5 times. Alternatively, two or more controlled flow, hydrodynamic cavitation apparatuses can be positioned in series to produce a multi-pass cavitation process.

The treated biosolids sludge 3 can flow into a condenser device 5 to form a sludge mixture 6, where steam may be continuously added to the condenser device. Steam 4 is added to the condenser device, which is based on an amount of sludge that enters the condenser device. A series of injection nozzles may be used to add steam to the condenser device. As the sludge mixture travels through the condenser device, steam may condense, which may transfer heat to the sludge mixture to increase temperature so that thermal hydrolysis may occur. Although not shown, the sludge mixture 6 may pass through a mixer device, such as a static mixer, to ensure that heat is evenly distributed throughout the sludge mixture. The mixer device may also mix any steam that has not yet condensed.

After the sludge mixture 6 is at a suitable temperature for thermal hydrolysis, the sludge mixture may enter a thermal hydrolysis reactor 8 and flow at a low velocity to form a hydrolyzed sludge 10. The hydrolyzed sludge 10 may result in plug flow, which ensures there is no short-circuiting and the hydrolyzed sludge is under thermal hydrolysis conditions for the required amount of time of approximately 30 minutes or more. The temperature within the reactor is approximately 150 to 180° C. and at a pressure in the range of 120-150 psi. The percent of dry solids may be approximately 20% w/w.

After the thermal hydrolysis reactor 8, the hydrolyzed sludge 10 may optionally enter a heat exchanger system 12 to cool the hydrolyzed sludge 10 to a lower temperature, for example, between 60 to 100° C. The heat exchanger system 12 can be shell and tube design or other conventional device as known in the art. The percent of dry solids may be approximately 20% w/w. The cooled hydrolyzed sludge 14 can optionally pass through a controlled flow, hydrodynamic cavitation apparatus 16 before being combined and mixed with dilution water 20.

The controlled flow, hydrodynamic cavitation apparatus 16 can be operated as described above, either alone or in combination with apparatus 2 to initially or further treat biosolids sludge as desired. The sludge 18 leaving the controlled flow, hydrodynamic cavitation apparatus 16, a treated biosolids sludge, can be mixed with dilution water 20 to form a diluted biosolids sludge stream 24, for example, dilution water can be mixed with a mixer device 22 such as an in-line static mixer. The dilution water may be used to dilute and cool the sludge 18. Optionally, the hydrolyzed sludge may pass through a pressure holding pump, which may be used to maintain pressure (not shown). The temperature of the hydrolyzed sludge may continue to decrease to approximately 35 to 60° C., and the percent of dry solids may be approximately 8-15% w/w.

The diluted biosolids sludge stream 24 can also optionally pass through a controlled flow, hydrodynamic cavitation apparatus 26 before being subjected to anaerobic digestion. The controlled flow, hydrodynamic cavitation apparatus 26 can be operated as described above, either alone or in combination with apparatuses 2, 16 to initially or further treat biosolids sludge as desired. The sludge 28 leaving the controlled flow, hydrodynamic cavitation apparatus 26, a treated biosolids sludge, can be subjected to further processing steps such as anaerobic digestion, to produce biogas and useful biosolids.

Figure 2:
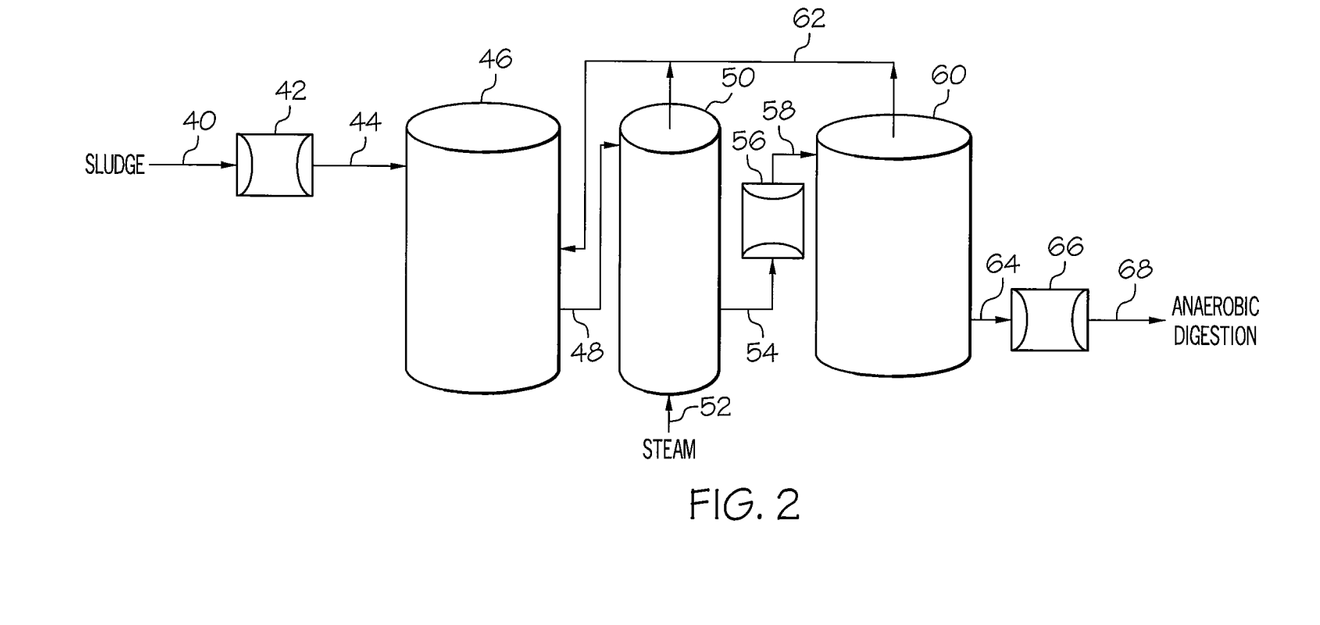
FIG. 2 is a flow diagram of a biosolids sludge treatment system utilizing thermal hydrolysis and hydrodynamic cavitation.

In another process, biosolids sludge can be treated with one or more controlled flow, hydrodynamic cavitation apparatuses in a batch process utilizing thermal hydrolysis. FIG. 2 shows a batch process for treating biosolids sludge. As shown, biosolids sludge 42 may be fed into a pulper 46 to be mixed and heated by recycled steam 62 generated from the thermal hydrolysis process, which can last for approximately 1.5 hours. The temperature in the pulper 46 can be approximately 100° C. The pulper 46 can use pumps, such as a recirculation pump, to mix the biosolids sludge. Prior to the biosolids sludge 40 entering the pulper 46, the sludge can be passed through a controlled flow, hydrodynamic cavitation apparatus 42, which will dissociate dewatered sludge molecules while increasing localized temperature and pressure and break up materials and increase available sites for reaction under thermal hydrolysis. The controlled flow, hydrodynamic cavitation apparatus 42, in addition to the other controlled flow, hydrodynamic apparatuses 56, 66 as shown in FIG. 2, preferably are the same as described above with regard to FIG. 1. The controlled flow, hydrodynamic cavitation apparatus 42 can be operated under the same parameters as above to form a treated biosolids sludge 44 that can be sent to the pulper. Apparatuses 56 and 66 also can be operated under the same parameters as above.

Following the pulper, the sludge 48 enters a thermal hydrolysis reactor 50 through a batch process. However, multiple reactors may be used to create a continuous process from the dewatering to the anaerobic digestion steps. Additional steam 52 may be added to increase the temperature and pressure within the batch reactor 50. For thermal hydrolysis to take place, the temperature within the reactor must reach 165° C. at a pressure near 70-100 psi to form a hydrolyzed biosolids sludge stream 54. Steam within the reactor is gradually released and transferred to the pulper 46 by a recirculation stream.

Following the reactor 50, the hydrolyzed biosolids sludge 54 may be passed through a second controlled flow, hydrodynamic cavitation apparatus 56 to further breakdown particles in the hydrolyzed sludge. The controlled flow, hydrodynamic cavitation apparatus 56 can be used in combination with apparatus 42, or separately in the batch process as the sole cavitation apparatus to initially or further treat biosolids sludge as desired.

The hydrolyzed sludge 58 discharged from the apparatus 56 may enter a flash tank 60 to reduce pressure, which is used to release steam 62 in the hydrolyzed sludge. Inside the flash tank 60, the cellular components in the hydrolyzed sludge 58 are further broken down. The temperature of the hydrolyzed sludge 28 is decreased to approximately 100° C. or below. After exiting the flash tank 60, the hydrolyzed sludge 64 may enter a third controlled flow, hydrodynamic cavitation apparatus 66. The controlled flow, hydrodynamic cavitation apparatus 66 can be used in combination with apparatuses 42 or 56, or separately in the batch process as the sole cavitation apparatus to initially or further treat biosolids sludge as desired.

The hydrolyzed sludge 68 discharged from the apparatus 66 may, a treated biosolids sludge, can be subjected to further processing steps such as anaerobic digestion, to produce biogas and useful biosolids. In addition to using controlled flow, hydrodynamic cavitation apparatuses to treat biosolids sludge, streams containing only enzymes may flow through additional controlled flow cavitation devices during the thermal hydrolysis process.

In order to promote a further understanding of the invention, the following examples are provided. These examples are shown by way of illustration and not limitation. It is shown by the examples that cavitation can reduce particle size of bio-solids, increase biogas production and increase volatile solids reduction.

Example

Bisolids sludge was treated by a controlled flow, hydrodynamic cavitation apparatus. As a baseline, a control sample was not subjected to the cavitation process.

Nine samples of biosolids sludge at a temperature in the range of 21 to 25° C. were passed through a local constriction in a controlled flow, hydrodynamic cavitation apparatus to induce a cavitation zone containing cavitation bubbles downstream of the local constriction. The bubbles were collapsed under a static pressure of 30 psi. The local constriction was a 5 mm diameter orifice.

Three samples of biosolids sludge were pressurized to 100 psi and passed through the cavitation apparatus. The pressure drop across the local constriction was 70 psi for each pass. One sample was passed through the cavitation apparatus once, 100-1, one sample was passed through twice, 100-2, and the last sample was passed through three times, 100-3.

Three samples of biosolids sludge were pressurized to 200 psi and passed through the cavitation apparatus. The pressure drop across the local constriction was 170 psi for each pass. One sample was passed through the cavitation apparatus once, 200-1, one sample was passed through twice, 200-2, and the last sample was passed through three times, 200-3.

Three samples of biosolids sludge were pressurized to 300 psi and passed through the cavitation apparatus. The pressure drop across the local constriction was 270 psi for each pass. One sample was passed through the cavitation apparatus once, 300-1, one sample was passed through twice, 300-2, and the last sample was passed through three times, 300-3.

Figure 3:
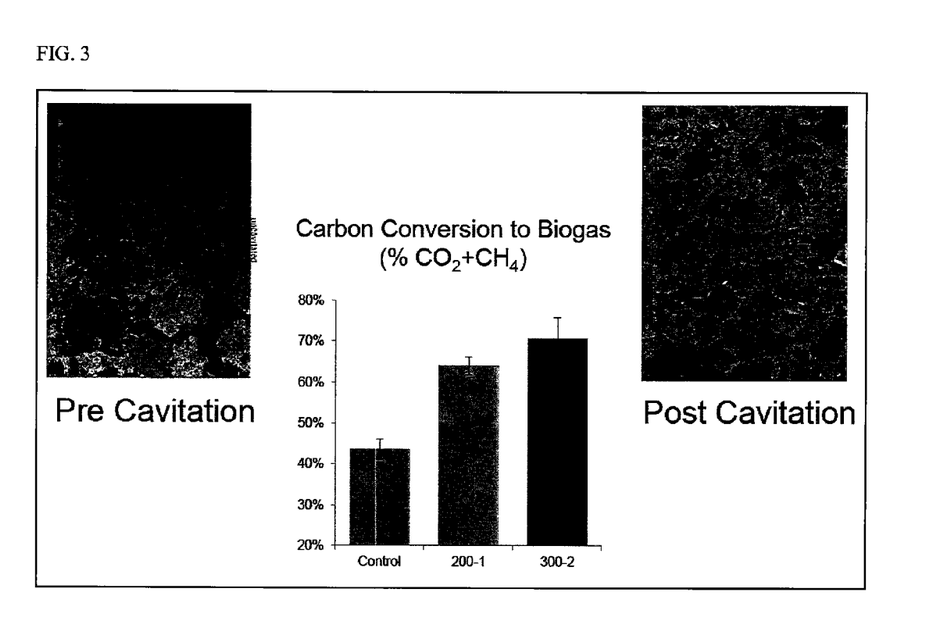
FIG. 3 shows photographs of biosolids sludge in the uncavitated or pre-cavitation state and the post cavitation state.
Figure 4:
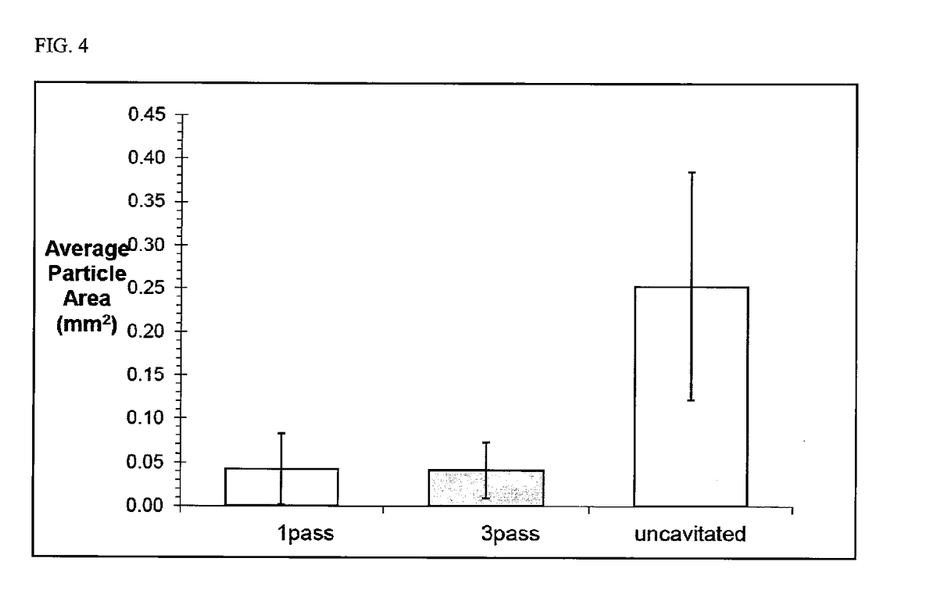
FIG. 4 is a graph illustrating the average particle size are reduction resulting from a single pass and a multi-pass hydrodynamic cavitation of biosolids sludge as compared to an uncavitated or pre-cavitation biosolids sludge sample.

FIG. 3 shows the particle make up of uncavitated biosolids sludge (pre-cavitation) and treated biosolids sludge after being passed through the controlled flow, hydrodynamic cavitation apparatus. FIG. 4 shows the reduction in the average particle size area, mm$^2$, that results from one pass and three passes of the biosolids sludge through the controlled flow, hydrodynamic cavitation apparatus. Uncavitated biosolids sludge measured an average particle area of 0.26 mm$^2$, whereas one pass and three passes through the cavitation apparatus reduced the average particle area to 0.04 mm$^2$. This resulted in a reduction of average particle area of 85%. Passing the biosolids sludge through the local constriction of a controlled flow, hydrodynamic cavitation apparatus preferably lowers or reduces the average particle area of biosolids sludge at least 50, 60, 70, 80, 90 or 95 percent as compared to uncavitated biosolids sludge.

Figure 5:
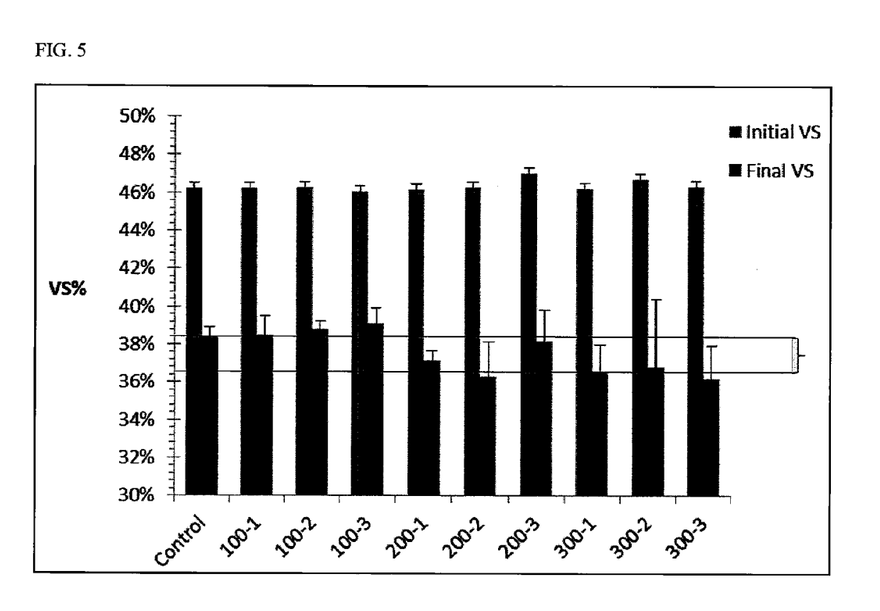
FIG. 5 is a graph illustrating the volatile solids reduction resulting from single pass and multi-pass hydrodynamic cavitation of biosolids sludge as compared to an uncavitated or pre-cavitation biosolids sludge sample.

FIG. 5 shows the reduction in the percent of volatile solids in uncavitated biosolids sludge (pre-cavitation) and treated biosolids sludge after being passed through the controlled flow, hydrodynamic cavitation apparatus and processed by anaerobic digestion. Uncavitated biosolids sludge processed by anaerobic digestion had a final volatile solids percent of 38.4. Biosolids sludge at a processing pressure of 200 psi being passed through the local constriction of a controlled flow, hydrodynamic cavitation apparatus resulted in a reduction in the range of 1 to 6.2 percent. One pass, 200-1, had a volatile solids percent of 37.2 (3.1 percent reduction), two passes had 36 (6.2 percent reduction) and three passes had 38 (1 percent reduction). Biosolids sludge at a processing pressure of 300 psi being passed through the local constriction of a controlled flow, hydrodynamic cavitation apparatus resulted in a reduction in the range of 4.7 to 6.2 percent. One pass, 300-1, had a volatile solids percent of 36.4 (5.2 percent reduction), two passes had 36.6 (4.7 percent reduction) and three passes had 36 (6.2 percent reduction). Passing the biosolids sludge through the local constriction of a controlled flow, hydrodynamic cavitation apparatus preferably lowers or reduces the percentage of volatile solids in the biosolids sludge after being processed by anaerobic digestion by at least 1, 2, 3, 4, 5, 6 or 7 percent as compared to uncavitated biosolids sludge.

Figure 6:
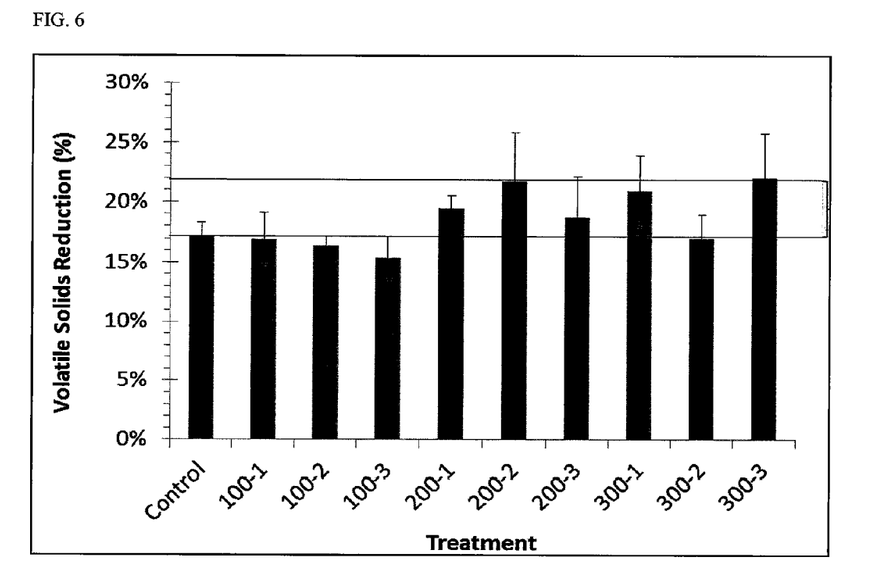
FIG. 6 is a graph illustrating the volatile solids reduction resulting from single pass and multi-pass hydrodynamic cavitation of biosolids sludge as compared to an uncavitated or pre-cavitation biosolids sludge sample.

FIG. 6 shows percentage of reduction in volatile solids from the samples discussed in FIG. 5. As shown, the samples cavitated at a processing pressure of 200 and 300 psi resulted, on average, in a reduction of volatile solids in the biosolids sludge as compared to the control, uncavitated sample.

Figure 7:
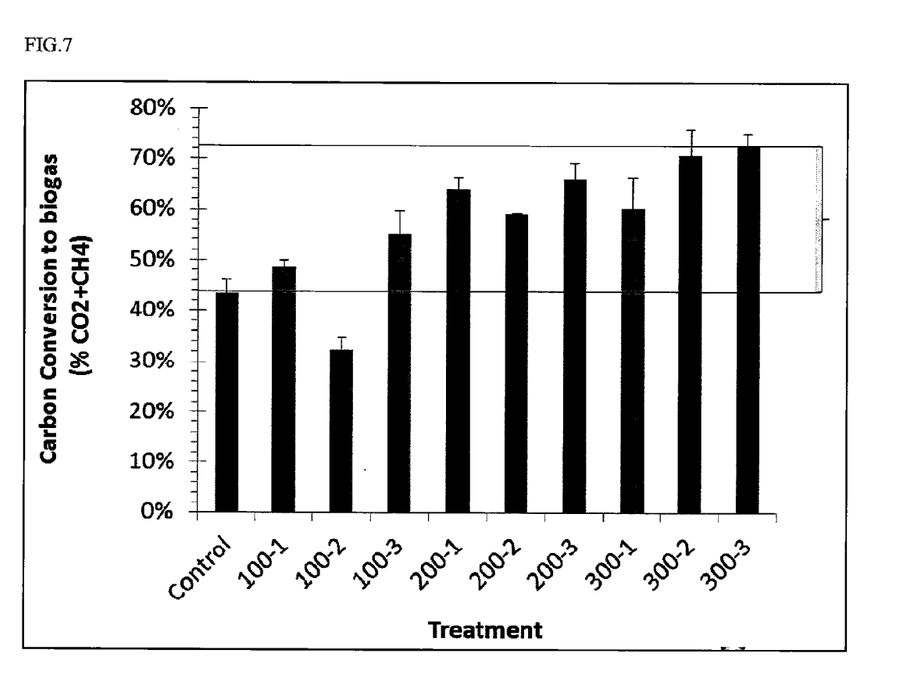
FIG. 7 is a graph illustrating the biogas production increase from single pass and multi-pass hydrodynamic cavitation of biosolids sludge as compared to an uncavitated or pre-cavitation biosolids sludge sample.

FIG. 7 shows the increase in carbon conversion to biogas in uncavitated biosolids sludge (pre-cavitation) and treated biosolids sludge after being passed through the controlled flow, hydrodynamic cavitation apparatus and processed by anaerobic digestion. Uncavitated biosolids sludge (control) processed by anaerobic digestion had a carbon conversion to biogas, measured as percentage of $CO_2$ and $CH_4$, of 44 percent. Biosolids sludge at a processing pressure of 100 psi being passed once (100-1) through the local constriction of a controlled flow, hydrodynamic cavitation apparatus resulted in a biogas production of 48 percent (9.1 percent increase). Three passes (100-3) at a processing pressure of 100 psi resulted in a biogas production of 55 percent (25 percent increase). Biosolids sludge at a processing pressure of 200 psi being passed through the local constriction of a controlled flow, hydrodynamic cavitation apparatus resulted in a biogas production in the range of 34.1 to 50 percent. One pass, 200-1, had a biogas percent of 64 (45.4 percent increase), two passes had 59 (34.1 percent increase) and three passes had 66 (50 percent increase). Biosolids sludge at a processing pressure of 300 psi being passed through the local constriction of a controlled flow, hydrodynamic cavitation apparatus resulted in a biogas production in the range of 38.6 to 63.6 percent. One pass, 300-1, had a biogas percent of 61 (38.6 percent increase), two passes had 70 (59.1 percent increase) and three passes had 72 (63.6 percent increase). Passing the biosolids sludge through the local constriction of a controlled flow, hydrodynamic cavitation apparatus preferably increases the percentage of biogas produced from the biosolids sludge after being processed by anaerobic digestion by at least 5, 10, 15, 20, 30, 40, 50, 60 or 65 percent as compared to uncavitated biosolids sludge.

It should now be apparent that there has been provided, in accordance with the present invention, a novel process for enhancing alcohol production by utilizing conventional starch by-products that satisfies the benefits and advantages set forth above. Moreover, it will be apparent to those skilled in the art that many modifications, variations, substitutions and equivalents for the features described above may be effected without departing from the spirit and scope of the invention. Accordingly, it is expressly intended that all such modifications, variations, substitutions and equivalents which fall within the spirit and scope of the invention as defined in the appended claims to be embraced thereby.

The preferred embodiments have been described, herein. It will be apparent to those skilled in the art that the above methods may incorporate changes and modifications without departing from the general scope of this invention. It is intended to include all such modifications and alterations in so far as they come within the scope of the appended claims or the equivalents thereof.

What is claimed is:

1. A method for increasing biogas yield in biosolids sludge comprising:
   a) providing a controlled flow hydrodynamic cavitation apparatus having a local constriction, the local constriction being an orifice, baffle or bluff body, and the hydrodynamic cavitation apparatus being a static cavitation apparatus;
   b) passing a stream of biosolids sludge at a processing pressure in the range of 200 to 1,000 psi and a temperature in the range of 10° to 60° C. through the local constriction of the controlled flow hydrodynamic cavitation apparatus to form a hydrodynamic cavitation zone downstream of the local constriction, the hydrodynamic cavitation zone containing cavitation bubbles, maintaining the cavitation bubbles in the hydrodynamic cavitation zone for less than 0.01 second, and the biosolids sludge being passed through the local constriction to create a pressure differential across the local constriction in the range of 150 to 850 psi;
   c) collapsing the cavitation bubbles under a static pressure in the range of 30 to 300 psi to form a treated biosolids sludge;
   d) subjecting the treated biosolids sludge to anaerobic digestion to produce an increased biogas yield, the biogas comprising carbon dioxide and methane,
   wherein the anaerobic digestion of the treated biosolids sludge subjected to steps b) and c) produces 25 to 65 percent more biogas than the same anaerobic digestion of an uncavitated portion of the stream of biosolids sludge not subjected to steps b) and c).

2. The method of claim 1, the biosolids sludge being at a pressure of at least 250 psi prior to passing through the local constriction.

3. The method of claim 1, the biosolids sludge being treated in the absence of ultrasonic cavitation.

4. The method of claim 1, the biosolids sludge being a dewatered biosolids sludge from a waterwork or wastewater treatment plant.

5. The method of claim 4, the dewatered sludge being subjected to thermal hydrolysis prior to being passed through the local constriction of the controlled flow, hydrodynamic cavitation apparatus.

6. The method of claim 1, the treated biosolids sludge being subjected to anaerobic digestion to reduce volatile solids in the treated biosolids sludge, wherein the treated biosolids sludge produces 2 to 7 percent less volatile solids as compared to untreated biosolids sludge being subjected to the anaerobic digestion.

7. A process for treating dewatered biosolids sludge from a waterwork or wastewater treatment plant, the process comprising:
   a) providing a static hydrodynamic cavitation apparatus having a local constriction, the local constriction being an orifice, baffle or bluff body;
   b) passing the dewatered biosolids sludge at a processing pressure in the range of 200 to 1,000 psi and a temperature in the range of 10 to 60° C. through the local constriction of the static hydrodynamic cavitation apparatus to form a hydrodynamic cavitation zone containing cavitation bubbles, maintaining the cavitation bubbles in the hydrodynamic cavitation zone for less than 0.01 second, the dewatered biosolids sludge being passed through the local constriction to create a pressure differential across the local constriction in the range of 150 to 850 psi;
   c) collapsing the cavitation bubbles downstream of the local constriction to form a treated biosolids sludge;
   d) subjecting the treated biosolids sludge to anaerobic digestion to produce an increased biogas yield, the biogas comprising carbon dioxide and methane,
   wherein the anaerobic digestion of the treated biosolids sludge subjected to steps b) and c) produces 25 to 65 percent more biogas than the same anaerobic digestion of an uncavitated portion of the dewatered biosolids sludge not subjected to steps b) and c).

8. The process of claim 7, the static hydrodynamic cavitation apparatus having at least two local constrictions in series, the dewatered biosolids sludge being passed through the at least two local constrictions.

9. The process of claim 7, the dewatered biosolids sludge being passed through the local constriction at least two times.

10. The process of claim 7, the treated biosolids sludge being subjected to thermal hydrolysis, anaerobic digestion or a combination of both.

11. The process of claim 10, the treated biosolids sludge being subjected to anaerobic digestion to reduce volatile solids in the treated biosolids sludge, wherein the treated biosolids sludge produces 2 to 7 percent less volatile solids as compared to untreated dewatered biosolids sludge being subjected to the anaerobic digestion.

12. The method of claim 1, the local constriction being an orifice, the orifice having a diameter in the range of 1 to 10 mm.

13. The method of claim 1, the biosolids sludge being passed through the local constriction not more than 1 pass.

14. The method of claim 1, the treated biosolids sludge is subjected to anaerobic digestion to produce biogas, the biogas comprising carbon dioxide and methane, wherein the treated biosolids sludge produces at least 30 percent more biogas as compared to uncavitated anaerobic digestion of biosolids sludge not subjected to steps b) and c).

15. The method of claim 7, the local constriction being an orifice, the orifice having a diameter in the range of 1 to 10 mm.

16. The method of claim 7, the biosolids sludge being passed through the local constriction not more than 1 pass.

\* \* \* \* \*